United States Patent [19]
Kirsch et al.

[11] Patent Number: 6,007,539
[45] Date of Patent: Dec. 28, 1999

[54] FASTENING NAIL

[75] Inventors: Axel Kirsch, Fildestadt; Dietmar Hutmacher, Freiburg, both of Germany

[73] Assignee: Axel Kirsch, Filderstadt, Germany

[21] Appl. No.: 09/101,847

[22] PCT Filed: Jan. 8, 1997

[86] PCT No.: PCT/DE97/00043
§ 371 Date: Nov. 25, 1998
§ 102(e) Date: Nov. 25, 1998

[87] PCT Pub. No.: WO97/26028
PCT Pub. Date: Jul. 24, 1997

[30]     Foreign Application Priority Data

Jan. 17, 1996 [DE] Germany ............................ 196 01 477

[51] Int. Cl.⁶ .................................................. A61B 17/84
[52] U.S. Cl. .................... 606/75; 606/72; 606/77
[58] Field of Search ................................. 606/75, 72, 73, 606/76, 77

[56]         References Cited

U.S. PATENT DOCUMENTS 4,898,186   2/1990   Ikada et al. .
5,492,452   2/1996   Kirsch et al. .

FOREIGN PATENT DOCUMENTS

0 202 090   11/1986   European Pat. Off. .
0 491 983    7/1992   European Pat. Off. .
43 00 039    6/1994   Germany .
43 08 239    6/1994   Germany .
WO92/15340   9/1992   WIPO .

*Primary Examiner*—Michael Buiz
*Assistant Examiner*—David O. Reip
*Attorney, Agent, or Firm*—Hill & Simpson

[57]                ABSTRACT

Fastening nail which is made of bioresorbable plastic material and is for the fixing of a covering membrane to an endogenous bone surrounding a bone void filled with bone replacement material, has a nail head of a larger diameter, enabling impact with a pressure and/or striking tool, and has, connected thereto, a nail shaft of a smaller diameter, which comprises an essentially cylindrical holder part and, connected thereto, a tip part with a jacket cone surface tapering in the direction towards the nail tip, the plastic material is at least partially non-crystalline (amorphous) and has a glass transition temperature in the region of body temperature, and the plastic material in the region of the nail shaft comprises a preferred molecular orientation that runs essentially parallel to the longitudinal axis of the fastening nail.

26 Claims, 8 Drawing Sheets

FASTENING NAIL

BACKGROUND OF THE INVENTION

The invention relates to a fastening nail made of bioresorbable plastic material for the fixing of a covering membrane to an endogenous bone surrounding a bone void filled with bone replacement material, having a nail head of larger diameter, enabling impact with a pressure and/or striking tool, and, connected thereto, a nail shaft of a smaller diameter, comprising an essentially cylindrical holder part and, connected thereto, a tip part having a jacket cone surface tapering in the direction towards the nail tip.

Known fastening nails of this type, whose structure is specified for example in DE-PS 43 00 039, are generally manufactured by the injection molding method, in such a way that the liquified thermoplastic plastic material is injected into the injection mold proceeding from the nail head.

Due to the unavoidable sprue, a burr thereby forms on the nail head, which must either be removed by means of expensive processing, or else, if it remains on the fastening nail for economic reasons, can lead to irritation of the soft tissue surrounding the nail head. In addition, the known fastening nails made of bioresorbable plastic material leave something to be desired with regard to their holding force in the bore made in the endogenous bone before their insertion.

SUMMARY OF THE INVENTION

The invention is based on the object of developing the fastening nail according to this generic type in such a way that an improved holding force results, whereby irritations of the soft tissue due to sprue formation on the nail head are moreover preferably avoided, and the manufacturing is to be simplified. In addition, in a particular embodiment of the fastening nail an improved applicability as a gingiva pin is also to be ensured.

According to the invention, this object is achieved in that the plastic material is at least partially non-crystalline (amorphous), and has a glass transition temperature in the region of body temperature, and in that the plastic material in the region of the nail shaft comprises a preferred molecular orientation that runs essentially parallel to the longitudinal axis of the fastening nail.

It can thereby be provided that the plastic material consists essentially of a linear polymer whose chain molecules in the region of the nail shaft run at least predominantly parallel to the longitudinal axis.

The invention also proposes that the plastic material is biologically decomposable.

In addition, it can be provided that the plastic material consists of a thermoplast.

In addition, the invention provides that the thermoplast comprises at least one polyester from the family of the poly-α-hydroxyl acids, such as polytrimethylene carbonate, polydioxone, polyglycolide, polylactide, poly(L-lactide-co-glycolide) together with other copolymers, polyorthoester and/or polycaprolactone (polyhydroxybuterate and polyhydroxybuterate-co-hydroxy valerate).

In addition, it can be provided that the glass transition temperature of the plastic material is approximately 37° C.

In addition, it can be provided that the plastic material contains bone replacement material.

The invention also proposes that the plastic material and/or the bone replacement material is/are mixed with growth factors.

It can thereby be provided that the plastic material is injected proceeding from the nail tip.

The invention also proposes that the cylinder projection is formed by the injection molding projection.

In addition, it can be provided that the tip part, connected to the sloped surface towards the nail tip, is provided with a cylinder projection.

In addition, the invention provides that the holder part is provided with an external threading at least over a part of its axial extension.

In addition, it can be provided that the holder part is provided at least over a part of its axial extension with at least one longitudinal slot, open towards the nail tip, and that the tip part is provided with at least one such slot, open towards the nail tip.

In addition, it can be provided that the jacket surface of the holder part is provided with holding projections at least over a part of its axial extension.

The invention also proposes that the holder part comprises a barrel-shaped convexity at least over a part of its axial extension.

It can thereby be provided that the nail head is fashioned with a lenticular shape, and is provided with a positively locking element for the application of a fastening tool that produces a torque.

The invention also proposes that a screw slot is provided as a positively locking element.

A particular embodiment of the inventive fastening nail for use as a gingiva pin is characterized in that, in a bearing region along one side of the longitudinal axis, the nail head has an axially greater thickness then in an overlap region situated diametrically opposite on the other side of the longitudinal axis.

It can thereby be provided that the head surface of the nail head is of convex construction in the bearing region and is fashioned concavely in the overlap region.

If warranted, the invention hereby also provides that the head surface of the nail head passes smoothly and continuously from the bearing region into the overlap region.

In addition, it can hereby be provided according to the invention that the bearing region and the overlap region of the nail head are respectively fashioned so as to be rounded off in the direction towards the underside of the nail head, facing the nail shaft.

In addition, it can be provided that the nail head goes over into the nail shaft via a spacer part having a diameter that is enlarged in relation to the nail shaft.

In addition, the invention provides that the spacer part tapers in essentially conical fashion from the nail head to the nail shaft.

It can thereby be provided that the spacer part comprises a jacket surface that is curved in essentially concave fashion.

The invention also proposes that a holding means is provided on the underside of the nail head facing the nail shaft, for the securing of mucus membranes or the like located between the bone and the nail head.

It can thereby be provided that the holding means comprises at least one holding spike.

The invention is based on the surprising finding that it is possible to produce a considerable improvement in the holding force of the known bioresorbable fastening nail, which is produced in one piece from plastic material and known as a minipin, by giving the chain molecules of the plastic material in the region of the nail shaft a preferred orientation parallel to the longitudinal axis of the fastening nail. This can take place either by placing already pre-oriented plastic material into a casting mold and subsequently pressing it with application of heat and pressure, or else by using a correspondingly modified injection molding method, in which the plastic compound is placed into the injection mold proceeding from the nail tip.

In addition, the glass transition temperature of the plastic material, which is at least partially non-crystalline, i.e. is either completely amorphous or partially crystalline, is selected in such a way that it is in the region of the body temperature of the person or of the animal in which the fastening nail is to be used. By this means, it is achieved that after insertion into the bore prepared in the bone, and when heated to body temperature, and the fastening nail expands radially in the region of the nail shaft by means of shrinkage in the direction of the longitudinal axis (=direction of flow in injection molding), as is known in the case of stretched polymers, whereby the holding force in the bore increases considerably.

If warranted, it is entirely possible, using the basic idea of the invention, to provide only a single ring shoulder on the cylindrical holder part of the fastening nail, further simplifying the manufacturing process, however it is of course also possible to provide several such ring shoulders.

The increased holding force in the bore in the endogenous bone as achieved by means of the invention is of particular advantage if the plastic material is interspersed with bone replacement material, since a particularly good contact with the endogenous bone, with correspondingly improved growth effects, then results here. This is particularly advantageous when the bone construction material is additionally mixed with growth factors, as is known from DE-PS 41 30 545 and from DE-PS 41 30 546.

The particular embodiment of the fastening nail according to the invention that is suitable for use as a gingiva pin enables, by means of the particular shaping of the nail head, with a thickened bearing region and a thinner overlap region, a particularly favorable drawing over and superposition of the various tissue layers, with a technique as described for example in Quintessenz 46, 975–984 (1995).

Further features and advantages of the invention result from the description of the preferred embodiment, claims and drawings.

Figure 1:
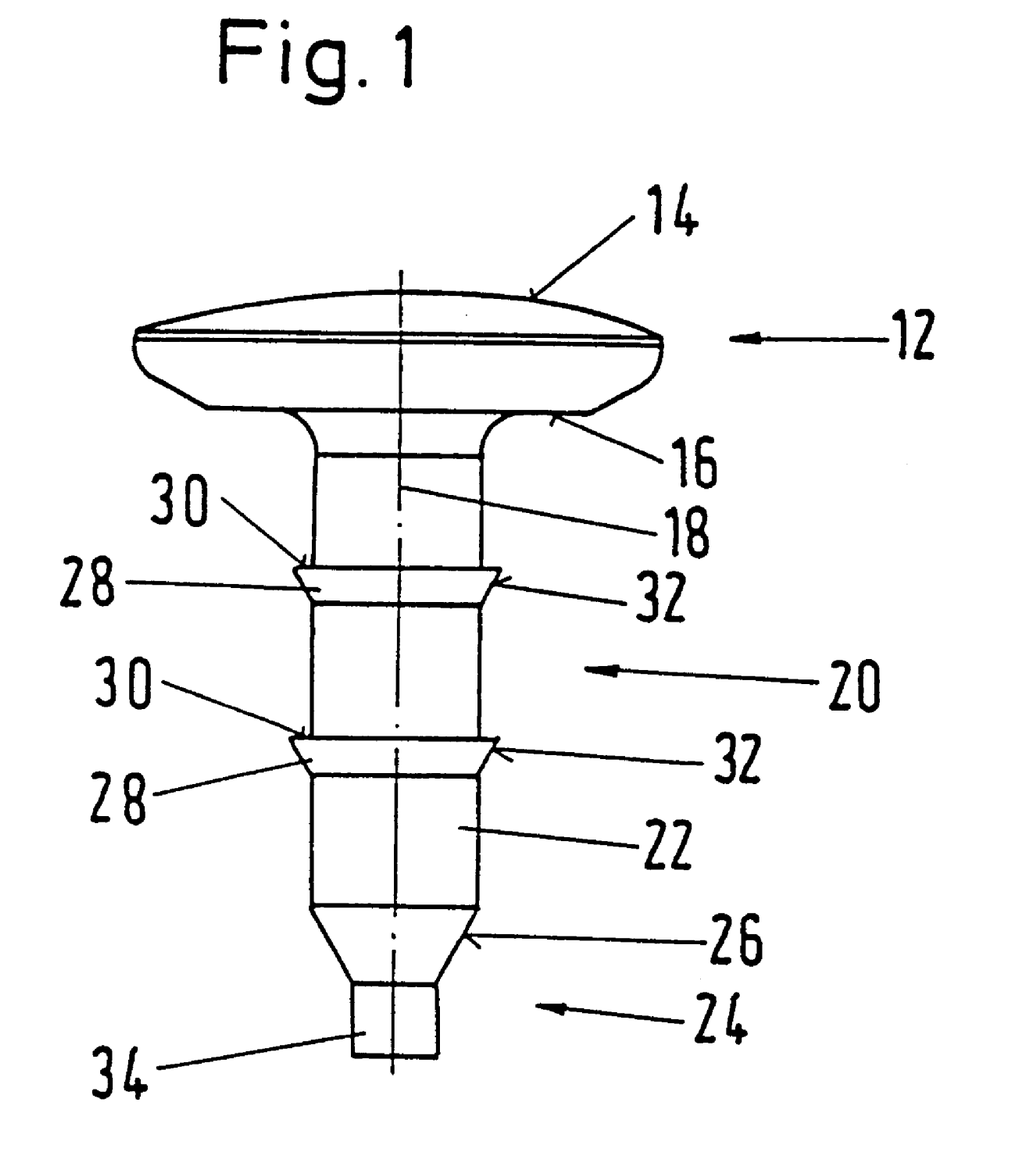
FIG. 1 is a side view of a first embodiment of the fastening nail of the present invention.

As FIG. 1 shows, the fastening nail according to the invention, in the embodiment there depicted, comprises a nail head 12 with a head surface 14 and a pressure surface 16, which are fashioned in rotationally symmetrical fashion with reference to a longitudinal axis 18 of the fastening nail, as are also all other components of the fastening nail to be described in the following. A nail shaft 20 comprises an essentially cylindrical holder part 22 and a tip part 24 fashioned in one piece herewith, and the cylindrical jacket surface of the holder part 22 is connected by a conical or cone surface 26 to the tip part 24. The cylindrical holder part 22 comprises two ring shoulders 28, which extend toward the jacket surface of the holder part 22 in the direction towards the nail head 12 with an annular surface 30 that runs essentially perpendicular to the longitudinal axis 18 on the one hand, and which pass over into the nail tip with a sloped surface 32 on the other hand. A cylinder projection 34 is connected to the cone surface 26 of the tip part 24 in the direction towards the nail tip, said cylinder projection simultaneously bounding this tip part.

In the embodiment shown, the manufacturing of the fastening nail ensues in that a liquefied thermoplastic plastic material, preferably a bioresorbable polymer material, is poured into a suitably constructed injection mold proceeding from the nail tip, whereby the chain molecules of the plastic material orient themselves essentially parallel to the longitudinal axis 18 of the fastening nail in the region of the nail shaft 20 or, respectively, of the holder part 22. The cylinder projection 34 is formed by the injection mold projection. After the formation of the fastening nail, this nail can be used without post-processing procedures, after sterilization, etc.

After the fastening nail has been inserted into a bore prepared in the endogenous bone, whereby the ring shoulders 28 deform elastically, so that the jacket surface of the holder part 22 already grips essentially tightly in the mentioned bore, the nail shaft 20 heats up to body temperature. The chain molecules of the plastic material, which are oriented parallel to the longitudinal axis 18, thereby attempt to draw together or, respectively, to shrink, with simultaneous radial extension of the nail shaft 20. By this means, the holding pressure inside the bore is increased in the sense of a press fit.

Figure 2:
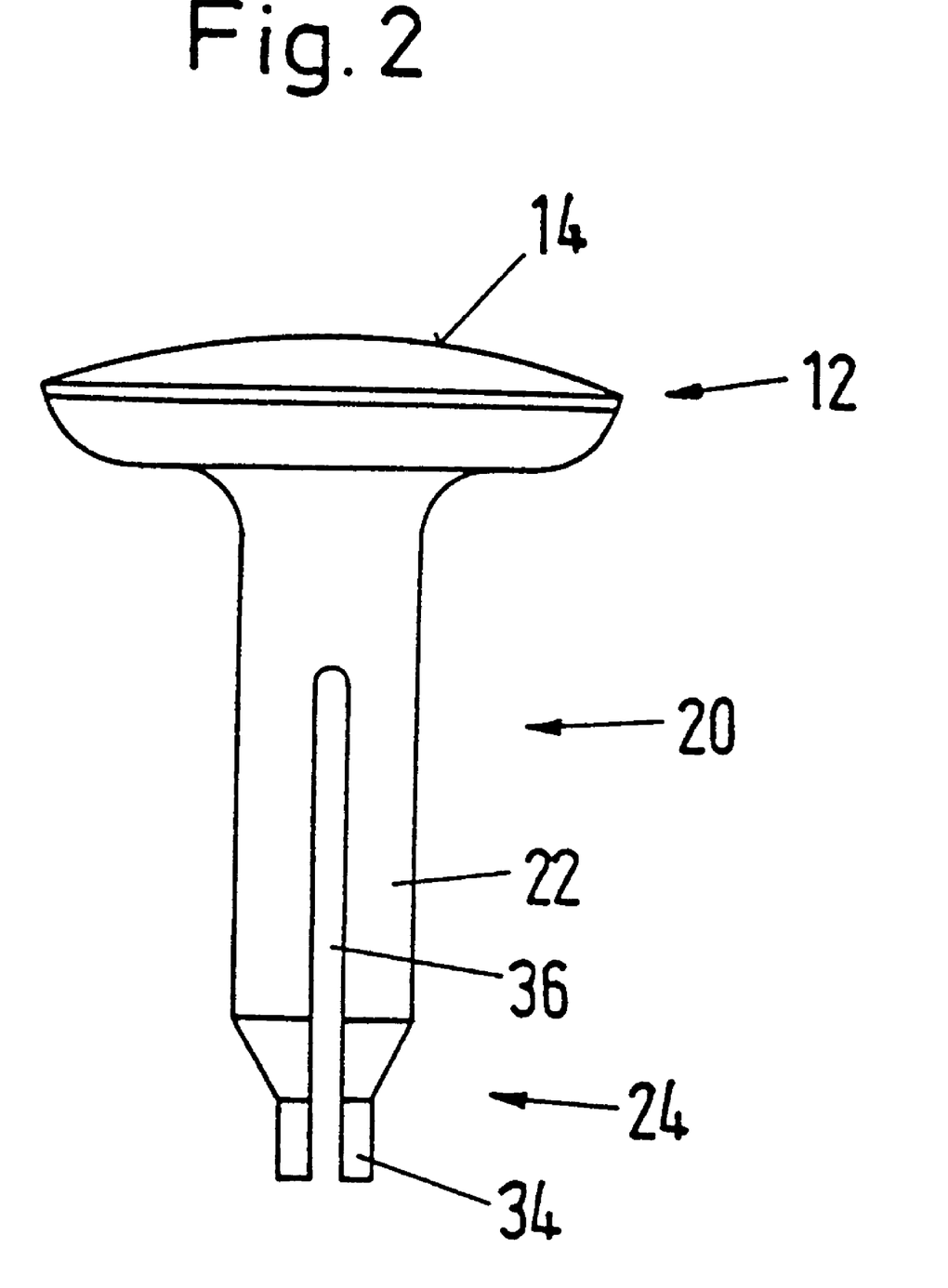
FIG. 2 is a side view of a second embodiment of an inventive fastening nail.

In the embodiment of FIG. 2, the holder part 22 comprises an axial longitudinal slot 36 over a portion of its axial longitudinal extension, which slot also goes through the tip part 24 and is open towards the nail tip, connected to the cylinder projection 34. During the driving of the fastening nail into the bone bore, the longitudinal slot 36 enables a resilient compression of the holder part 22 and a solid seating thereof in the bone bore.

Figure 3:
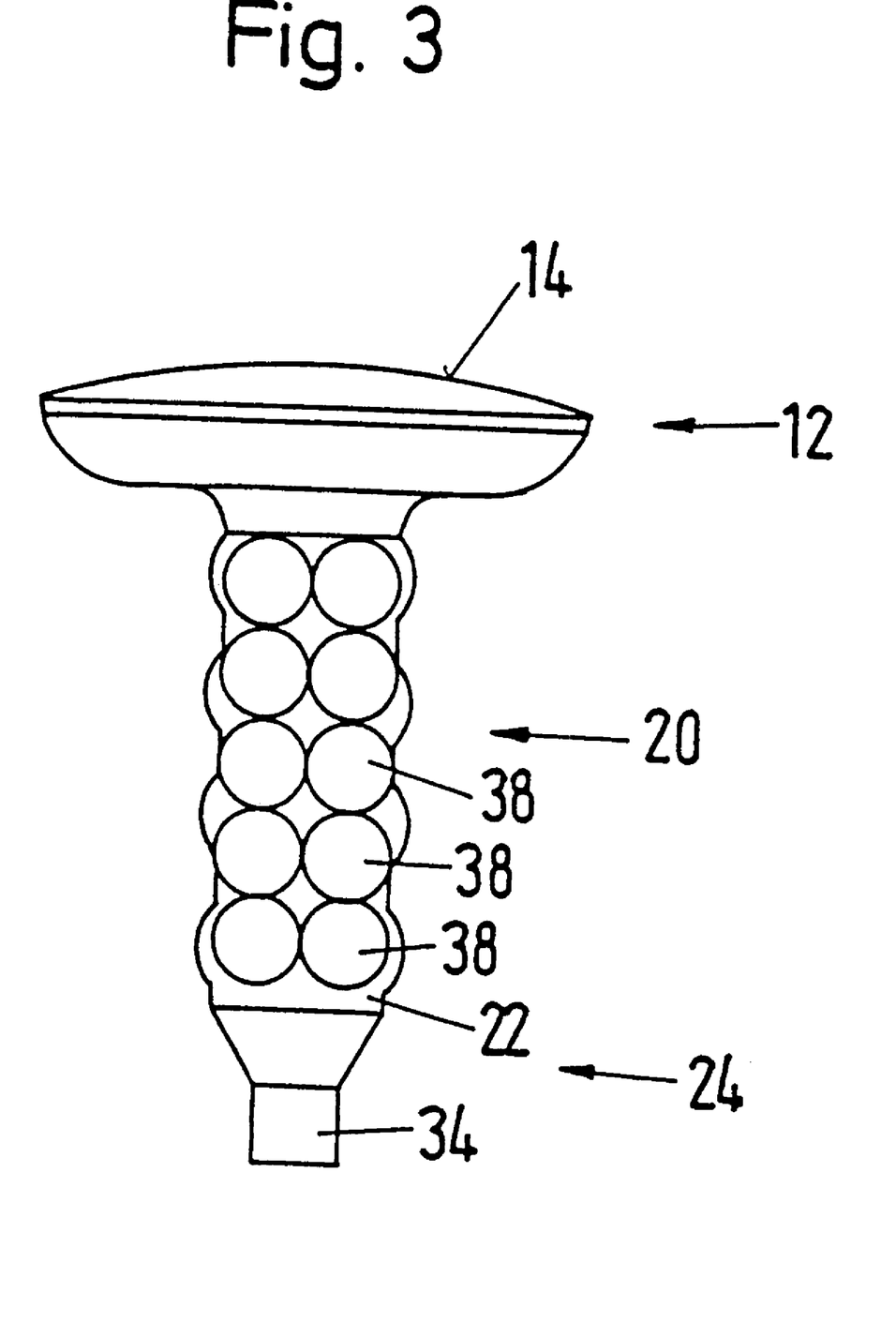
FIG. 3 is a side view of a third embodiment of a fastening nail according to the invention.

The embodiment of FIG. 3 is distinguished in that here the holder part 22 of the nail shaft 20 is provided with a row of holding projections 38, which are fashioned in the manner of culotte shells and are relatively flat. During the driving of the fastening nail into the bone bore, these projections can be pressed together slightly, by which means an unproblematic insertion and a good seating of the fastening nail in the bone bore are ensured.

Figure 4:
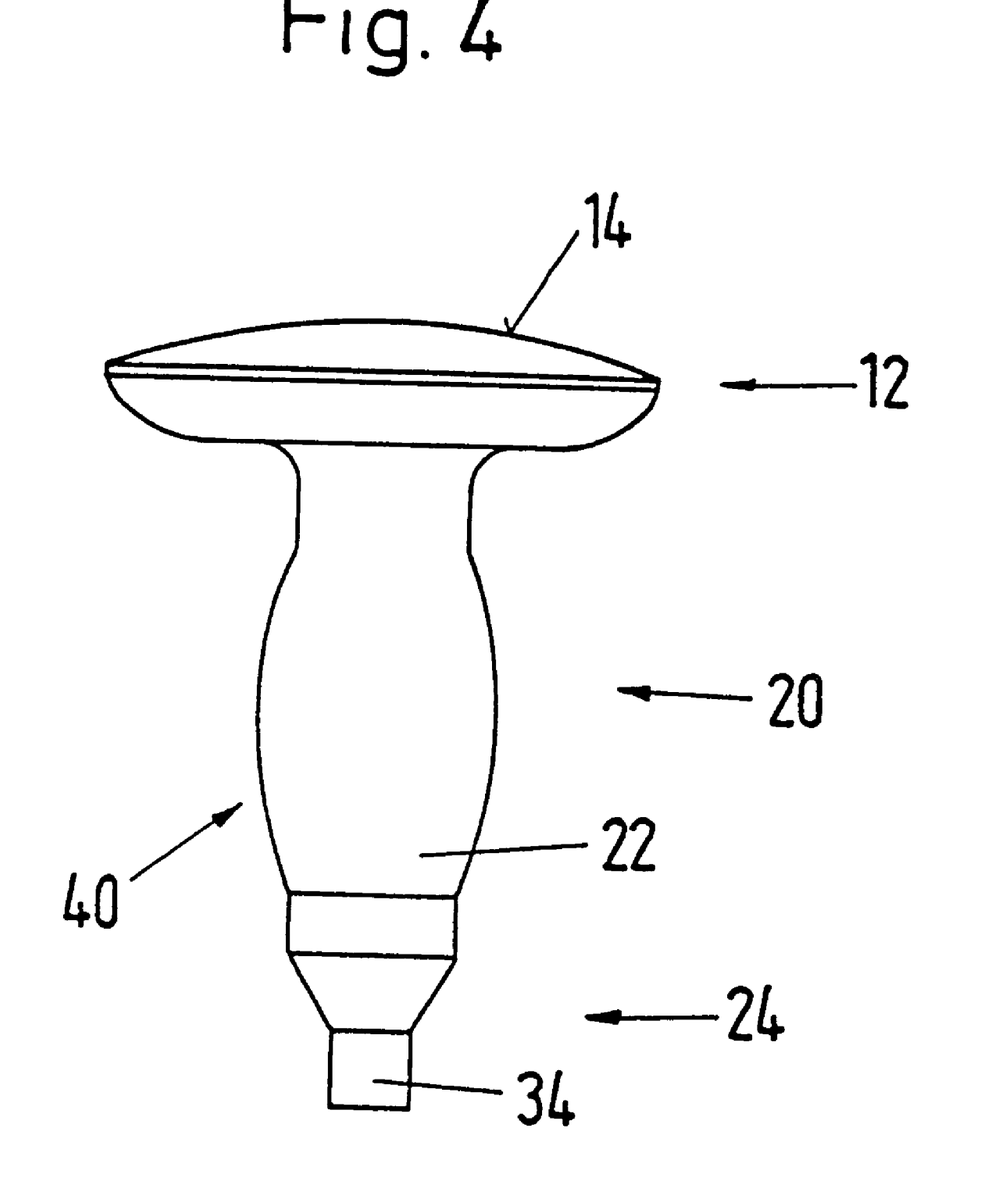
FIG. 4 is a side view of a fourth embodiment of a fastening nail according to the invention.

In the embodiment of FIG. 4, the holder part 22 of the nail shaft 20, which is in itself essentially cylindrical, is provided with a slight convexity 40, which, here as well, enables a slight compression of the nail shaft 20 during the driving of the fastening nail into the bone bore, simultaneously ensuring a solid pressure seating after the insertion of the fastening nail.

Figure 5:
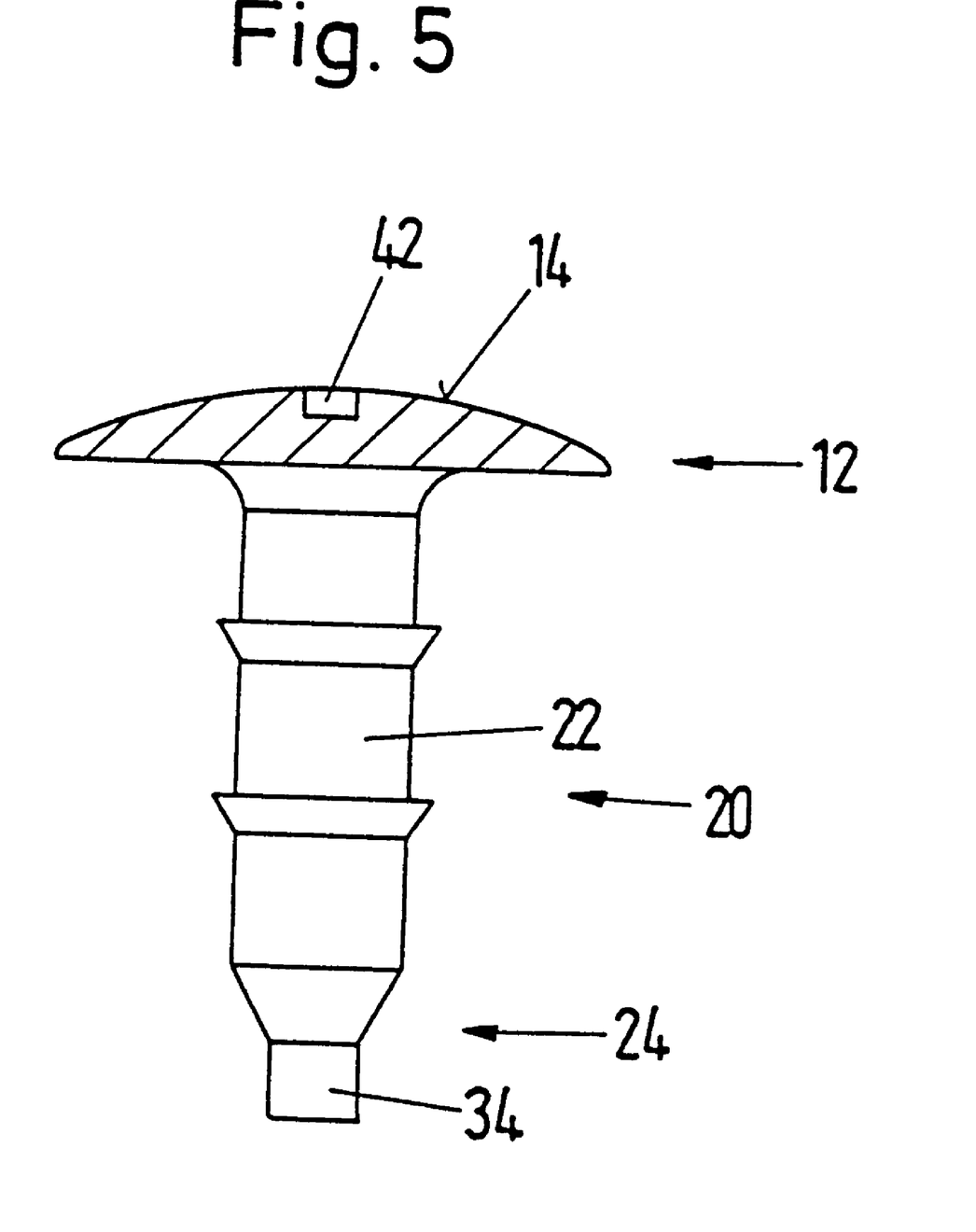
FIG. 5 is a side view of a fifth embodiment of a fastening nail according to the invention.

In the embodiment of FIG. 5, which in other respects corresponds to that of FIG. 1, the nail head 12 is of lenticular construction, and comprises a screw slot 42 for the application of a fastening tool, in particular of a screwdriver or the like that produces torque, whereby, of course, in place of a screw slot corresponding application elements for imbus wrenches, lug wrenches, or the like can also be provided.

Figure 6:
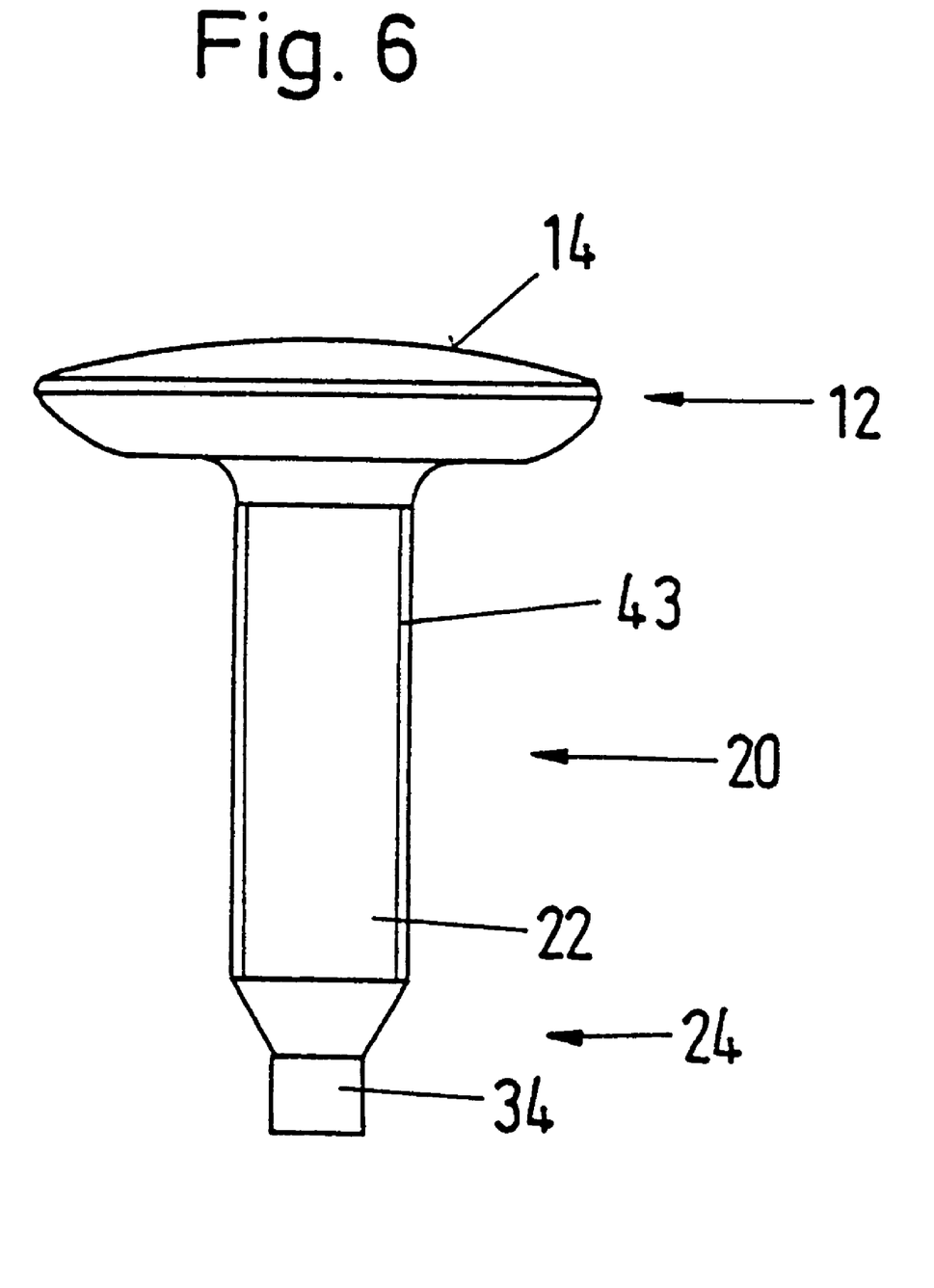
FIG. 6 is a side view of a sixth embodiment of a fastening nail according to the invention.

In FIG. 6, an embodiment of the fastening nail according to the invention is shown, in which the holder part 22 of the nail shaft 20 is provided with an outer threading 43, which ensures a rotational screwing of the fastening nail into a bone bore.

Figure 7:
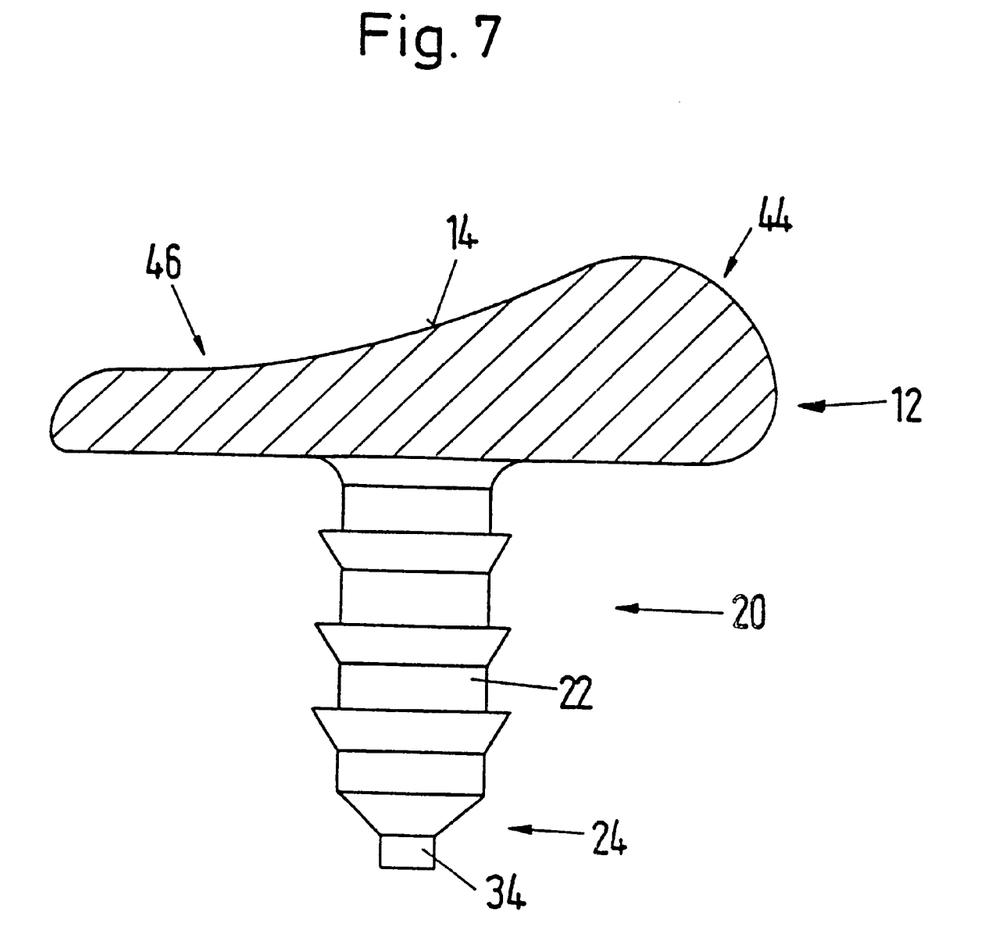
FIG. 7 is a side view with a portion in cross-section of a seventh embodiment of a fastening nail according to the invention, intended for use as gingiva pin.

The embodiment of the inventive fastening nail shown in FIG. 7 is provided for use as a gingiva pin. The construction of the nail shaft 20 thereby corresponds essentially to the embodiment of FIG. 1. For the nail head 12, it is characteristic that here (shown at right in FIG. 7) a bearing region 44 that is thickened in the axial direction is provided, and on the diametrally opposite side (shown at left in FIG. 7) an overlap region 46 that is thinner in the axial direction is provided. The head surface 14 is essentially concave in the overlap region 46 (seen in a top view from above) and is of essentially convex construction in the bearing region 44. Both the bearing region and also the overlap region 46 pass or extend over into the lower bearing surface (shown at bottom in FIG. 7) of the nail head 12 with a smooth rounding off. In addition, with respect to the head surface 14, the bearing region 44 and the overlap region 46 extend into one another smoothly and continuously.

Figure 8:
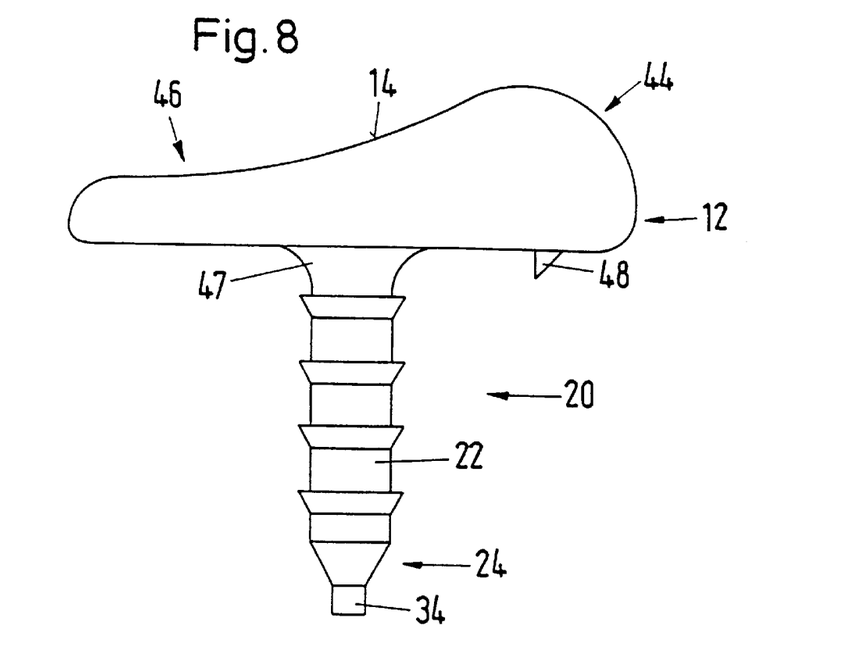
FIG. 8 is a side view of an eighth embodiment of a fastening nail according to the invention, intended for use a gingiva pin.
Figure 9:
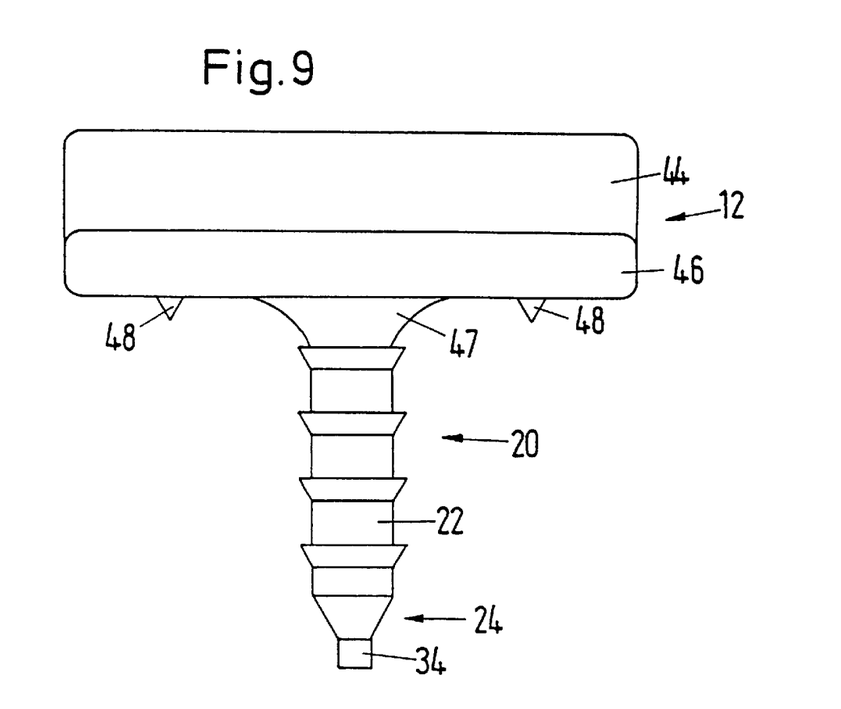
FIG. 9 is a side view of the nail of FIG. 8 rotated by 90°.

In the embodiment of FIGS. 8 and 9, which in other respects corresponds to that of FIG. 7, the nail head 12 extends into the nail shaft 20 via a spacer part 47, whose diameter is enlarged in relation to the nail shaft 20. The jacket surface of the spacer part 47 has the shape of a partial cone drawn inward concavely in the direction towards the longitudinal midaxis of the fastening nail. The height of the partial cone, seen in the direction of the longitudinal midaxis of the fastening nail, is approximately 1 mm. In addition, a series of holding spikes 48 are provided on the underside of the nail head in the embodiment of FIGS. 8 and 9. In place of the holding spikes 48, provided only at points in the embodiment shown, it is also possible to provide the entire underside of the nail head 46, facing the nail shaft 20, with a multiplicity of such holding spikes. It can also be provided that holding rails, which may be straight or also concentrically circumferential, are provided, whereby such holding means have in common that they are fashioned so as to be pointed in the direction towards the nail shaft 20.

The purpose of the spacer part 47 and of the holder spikes 48 is the following: By means of the spacer part 47, whose diameter is enlarged in relation to the nail shaft 20, it is achieved that the underside of the nail head 12 does not lie tightly on the endogenous bone; rather, an intermediate space of approximately 0.5 to 1 mm remains. By this means, a crushing of the mucous membrane located there is prevented. Nonetheless, the holder spikes 48 still ensure a reliable securing of the mucous membrane between the nail head 12 and the nail shaft 20.

The features of the invention disclosed in the preceding specification, in the drawing, and in the claims can be essential for the realization of the invention in its various embodiments both individually and also in arbitrary combinations.

We claim:

1. Fastening nail for the fixing of a covering membrane to an endogenous bone surrounding a bone void filled with bone replacement material, said nail comprising a nail head enabling impact with a pressure and/or striking tool, and having, connected thereto, a nail shaft of a smaller diameter than a diameter of the head, said shaft having an essentially cylindrical holder part and, connected thereto, a tip part with a jacket cone surface tapering in the direction towards the nail tip, the nail being made of a bioresorbable plastic material which is at least partially non-crystalline and amorphous, said material having a molecular orientation in the region of the nail shaft that runs essentially parallel to a longitudinal axis of the fastening nail, and the plastic material having a glass transition temperature in the region of the body temperature.

2. Fastening nail according to claim 1 wherein the plastic material essentially consists of a linear polymer whose chain molecules in the region of the nail shaft run at least predominantly parallel to the longitudinal axis.

3. Fastening nail according to claim 1 wherein the plastic material is biologically decomposable.

4. Fastening nail according to claim 1 wherein the plastic material is made of a thermoplast.

5. Fastening nail according to claim 4, wherein the thermoplast comprises at least one polyester from the family of the poly-α-hydroxyl acids, which include polytrimethylene carbonate, polydioxanone, polyglycolide, polylactide, poly(L-lactide-co-glycolide) together with other copolymers, polyorthoester and/or polycaprolactone (polyhydroxybuterate and polyhydroxybuterate-co-hydroxyvalerate).

6. Fastening nail according to claim 1, wherein the glass transition temperature of the plastic material is approximately 37° C.

7. Fastening nail according to claim 1 wherein the plastic material contains bone replacement material.

8. Fastening nail according to claim 7 wherein the plastic material and/or the bone replacement material is/are mixed with growth factors.

9. Fastening nail according to claim 1 wherein the plastic material is injected proceeding from the nail tip.

10. Fastening nail according to claim 9, which includes a cylinder projecting at the tip being formed by the injection molding.

11. Fastening nail according to claim 1, wherein the tip part is provided with a cylinder projection connected to an end of the cone surface.

12. Fastening nail according to claim 1 wherein that the holder part is provided with an outer threading at least over a part of its axial extension.

13. Fastening nail according to claim 1 wherein the holder part is provided, at least over a part of its axial extension, with at least one longitudinal slot open towards the nail tip, and the tip part is provided with at least one longitudinal slot, open towards the nail tip.

14. Fastening nail according to claim 1 wherein the jacket surface of the holder part is provided with holding projections at least over a part of its axial extension.

15. Fastening nail according to claim 1 wherein the holder part comprises a barrel-shaped convexity at least over a part of its axial extension.

16. Fastening nail according to claim 1 wherein the nail head has a lenticular shape, and is provided with a positively locking element for the application of a fastening tool that produces torque.

17. Fastening nail according to claim 16 wherein a screw slot is provided as a positively locking element.

18. Fastening nail according to claim 27, wherein the nail is used as a gingiva pin, and has a bearing region located on one side of the longitudinal axis with the nail head having an axially larger thickness than in an overlap region located in a diametrically opposed fashion on the other side of the longitudinal axis.

19. Fastening nail according to claim 18, wherein the head surface of the nail head is of convex construction in the bearing region and is of concave construction in the overlap region.

20. Fastening nail according to claim 18 wherein the head surface of the nail head passes over smoothly and continuously from the bearing region into the overlap region.

21. Fastening nail according to claim 18 wherein in that the bearing region and the overlap region of the nail head are respectively fashioned so as to be rounded-off in the direction towards the underside of the nail head, facing the nail shaft.

22. Fastening nail according to claim 18 wherein the nail head passes over into the nail shaft via a spacer part that has a diameter that is enlarged in relation to that of the nail shaft.

23. Fastening nail according to claim 22, wherein the spacer part tapers in essentially conical fashion from the nail head to the nail shaft.

24. Fastening nail according to claim 22 the spacer part comprises a jacket surface that is curved in essentially concave fashion.

25. Fastening nail according to claim 22 wherein a holder means, for the securing of mucous membrane regions or the like located between the bone and the nail head, is provided on the underside of the nail head, facing the nail shaft.

26. Fastening nail according to claim 25, wherein the holder means comprises at least one holding spike.

* * * * *